United States Patent [19]
Garby et al.

[11] Patent Number: 5,638,970
[45] Date of Patent: Jun. 17, 1997

[54] CHILD-RESISTANT INDICATOR CAP

[75] Inventors: Gage L. Garby, Boulder, Colo.;
Homer J. Brown, Jr., Oreland, Pa.

[73] Assignee: Senetics, Inc., Boulder, Colo.

[21] Appl. No.: 33,881

[22] Filed: Mar. 19, 1993

Related U.S. Application Data

[63] Continuation-in-part of Ser. No. 718,354, Jun. 21, 1991, abandoned, which is a continuation-in-part of Ser. No. 641,759, Jan. 17, 1991, abandoned, which is a continuation-in-part of Ser. No. 306,485, Feb. 3, 1989, Pat. No. 5,009,338.

[51] Int. Cl.⁶ .................................................. B65D 55/02
[52] U.S. Cl. .......................... 215/219; 116/308; 116/312; 206/459.5; 206/534; 215/220; 215/230
[58] Field of Search ..................... 215/230, 218, 215/219, 220; 206/534, 459.5; 116/308, 311, 312

[56] References Cited

U.S. PATENT DOCUMENTS

| | | | |
|---|---|---|---|
| 2,964,207 | 12/1960 | Towns | 215/220 |
| 4,011,829 | 3/1977 | Wachsmann et al. | 116/121 |
| 4,365,722 | 12/1982 | Kramer | 215/220 |
| 4,528,933 | 7/1985 | Allen | 116/308 |
| 4,666,051 | 5/1987 | Trick | 215/230 |
| 5,009,338 | 4/1991 | Barker | 215/230 |
| 5,082,129 | 1/1992 | Kramer | 215/221 |
| 5,115,929 | 5/1992 | Buono | 215/220 |
| 5,184,739 | 2/1993 | Kusz | 215/220 |
| 5,197,616 | 3/1993 | Buono | 215/220 |
| 5,242,067 | 9/1993 | Garby et al. | 215/230 |
| 5,261,548 | 11/1993 | Barker et al. | 215/230 |

*Primary Examiner*—Allan N. Shoaf
*Assistant Examiner*—Robin A. Hylton
*Attorney, Agent, or Firm*—Davis, Graham & Stubbs LLP

[57] ABSTRACT

A closure for a container including an indicator mechanism to record the removal of the closure from the container and a child-resistant mechanism to resist the removal of the closure from the container by a child. A spring in the indicator mechanism urges the indicator mechanism toward the child-resistant mechanism to provide sufficient force to engage the child-resistant mechanism for the attachment of the closure to the container, but not sufficient force to engage the child-resistant mechanism for the removal of the closure from the container, so that an additional external force must be applied to engage the child-resistant mechanism for the removal of the closure from the cap. The additional, external force is also necessary to engage the indicator mechanism, so that the mechanism cannot be inadvertently advanced.

13 Claims, 2 Drawing Sheets

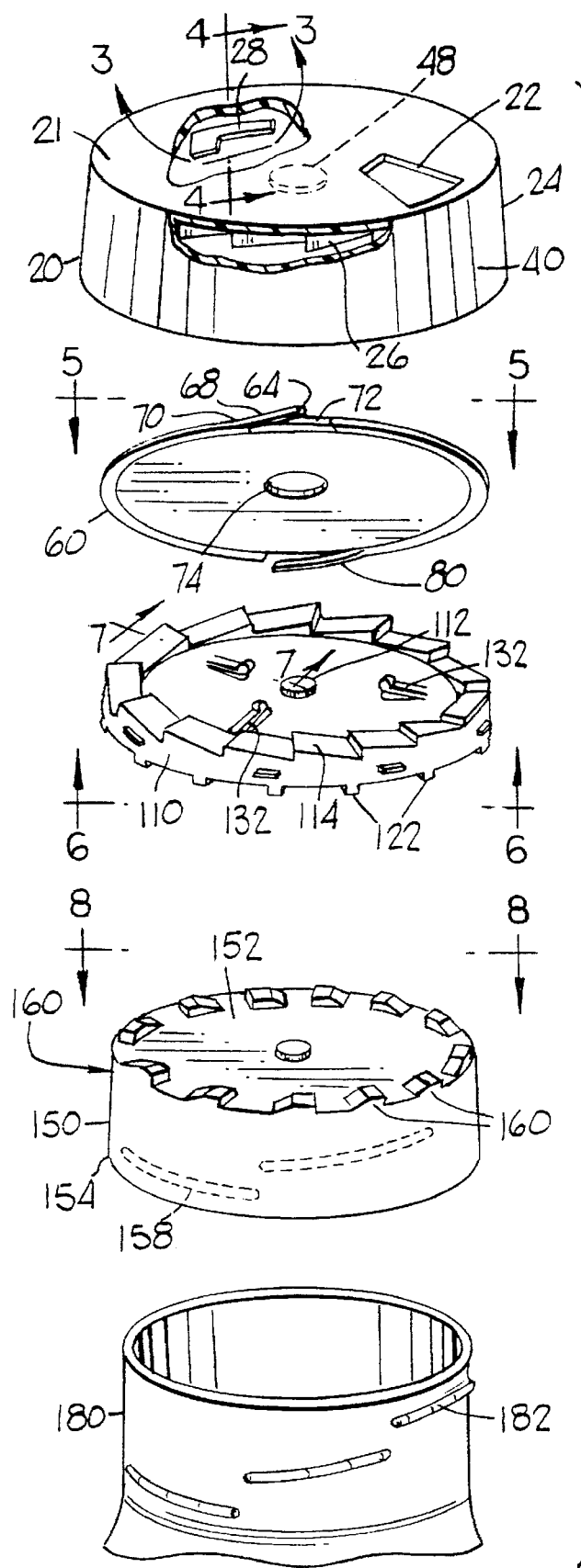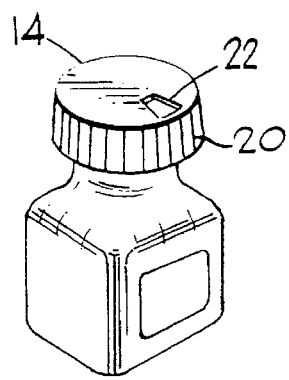
FIG.1
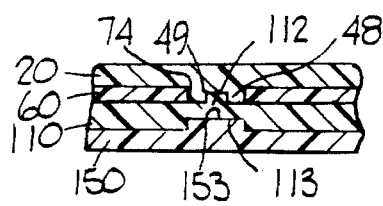
FIG.2A
FIG.2
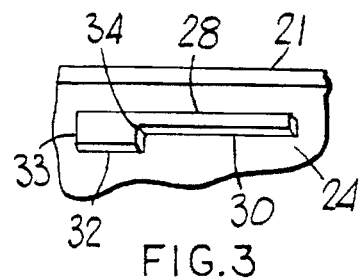
FIG.3
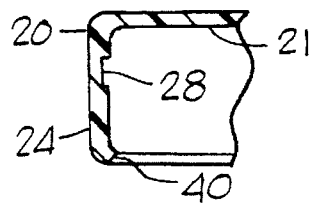
FIG.4

CHILD-RESISTANT INDICATOR CAP

This application is a continuation-in-part of application Ser. No. 07/718,354, now abandoned filed Jun. 21, 1991, which is a continuation-in-part of application Ser. No. 07/641,759, now abandoned filed Jan. 17, 1991, which is a continuation-in-part of application Ser. No. 07/306,485 filed Feb. 3, 1989 (now issued as U.S. Pat. No. 5,009,338). The disclosures of the parent applications are hereby incorporated herein by this reference.

BACKGROUND OF THE INVENTION

The present invention relates to closure members for containers, bottles and the like and, more particularly, to closure members having indicator means to indicate the number of times the container has been opened. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, over-utilization may cause side effects or toxicity to a much greater extent than any possible benefit. Thus it is critically important that a patient follow prescribed directions on medications, yet frequently patients forget whether they have taken medication and either omit doses or repeat them.

A considerable number of pill-timing schemes have been used to solve the problem of reminding a patient to take a dose of medicine or reminding him that he has already taken the dose. The most common ones involve some scheme of compartmentalization of the necessary medication, such that the pills are placed in compartments that are labeled by day, dose number or time of day, or that are serially numbered. These devices are reasonably satisfactory if a responsible person is available and has the time and patience to fill the compartments properly.

In dispensing pills of a single type, a number of bottle caps have been invented having a window through which an index symbol is visible. In only a few devices does the indicating element index in position relative to the window each time the cap is loosened, removed, replaced, and re-tightened. Thus, by looking at the index mark displayed through the window, a user can see where in repetitive sequence of dose he or she is.

One of the most serious disadvantages of prior art devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users, especially the elderly who may not understand how the device operates, will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. No. 4,011,829 issued Mar. 15, 1977 to Wachsmann, et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of a complicated "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

The device of European Patent Application No. 87100917.2, published Jul. 27, 1987, by Schwab, has a cup-shaped exterior element that engages a frustoconical closure cap. The Schwab device is somewhat complicated in design and manufacture. The device of U.S. Pat. No. 4,220,247 issued Sep. 2, 1980 to Kramer also includes a cup-shaped exterior element which engages an inner element. It appears that Wachsmann, Livingston, Trick and Schwab all utilize an ordinary symbol arrangement which is usable only with a single dosing regimen.

Other devices in the art include U.S. Pat. Nos. 4,511,050 by Nicol; 4,365,722 by Kramer; 4,749,093 by Trick; 4,782,966 by Thackrey; 4,753,189 by Mastman; 4,705,182 by Newel-Lewis; 4,662,520 by Griffen; 4,641,759 by Kelley; 4,634,012 by Kelley; 4,562,933 by Dennis; 4,528,933 by Allen; 4,511,050 by Nicol; 4,548,157 by Hevoyan; 4,501,370 by Kelley; 4,489,834 by Thackrey; 4,432,300 by Lyss; 4,419,016 by Zoltan; 4,405,045 by Villa-Real; 4,357,192 by Moser; 4,347,804 by Villa-Real; 4,094,408 by Ford; 3,996,879 by Walton; 3,960,713 by Carey; 3,926,326 by Grau; 3,921,568 by Fish; 3,887,099 by Gillman; 3,753,417 by Garby; 3,446,179 by Bender; 3,334,731 by Dale; 2,943,730 by Tregilgas; 2,939,597 by Greene; 2,587,147 by Guion; and 498,851 by Adsit.

The parent applications mentioned at the outset disclose devices for indicating the number of times a closure has been removed from a container or indicating compliance with a dosing schedule, wherein the device can be advanced only a single symbol at a time and wherein the advancement is affirmatively indicated to the user by an audible "click" when a pawl passes over a tooth in the mechanism. Such devices may be used in combination with child-resistant closures of the push and turn type in which to remove the closure from the container it is necessary to apply a force urging the closure toward the container simultaneously with a rotative force.

There is a need for an improved indicator cap in the manner of the present invention that prevents the device from being operated unless a force is applied urging the closure toward the container simultaneously with the application of a rotative force, so that the device is prevented from accidentally advancing. Such a device would be especially suitable for use with child-resistant closures of the push and turn type which require similar forces for removal of the closure from the container. Further, it would be desirable for such a device to provide an audible warning to a nearby adult in the event a child is attempting to remove the closure without applying the necessary force urging the closure toward the container. It would also be desirable for the closure to be replaceable onto the container without the need for such force, so that the closure is secured on the container even if the user is not careful about following a prescribed replacement procedure.

Additionally, there is a need for an indicator cap that provides positive controlled movement of the index on both opening and closing of the device, while also providing an indication to the user that the index has functioned properly each time the device is used. Preferably, the basic design of such a device can also be used in other applications where it is necessary to have a record of the number of times a given event occurs.

It is also apparent from a review of this art that there is a need for an improved indicator cap that can be used as a child-resistant closure. Preferably, such a cap would have a minimum of parts, would be easily manufactured and assembled using standard injection molding and assembly methods, and could be used with ordinary containers that are not necessarily specially designed for the cap.

SUMMARY OF THE INVENTION

It is an object of the present invention to provide an indicator device to indicate the number of times a given event has occurred. Such an invention may have applicability in the control of chemical containers, the development of photographic film and many other areas. More particularly, it is an object of the present invention to provide an indicator cap for a medication dispensing bottle or the like that provides an indication each time the bottle is opened and then reclosed.

It is a further object of the present invention to provide an indicator device in which the indicator symbols are not advanced except upon application of a force urging the closure toward the container simultaneously with a rotative force, so that the device is especially applicable to use with a child-resistant closure of the push and turn type which requires those same forces for removal of the closure from the container.

It is a further object of the invention to provide an indicator mechanism which resists accidental or inadvertent advancement, by requiring the application of a force urging the closure toward the container simultaneous with a rotative force when removing the mechanism from a container. Another object of the invention is to allow the closure to be replaced onto the container and to allow the indicator mechanism to be recocked without the necessity for the application of such force. Another object is to provide a closure in which an audible warning is sounded when the user attempts to remove the closure from a container without applying the requisite force urging the closure toward the container. For example, if a child attempts to remove the closure from a container without applying the requisite force, a warning will be sounded that is audible to a nearby adult. Another object is to allow the indicator mechanism to be set by applying the necessary force urging the closure toward the container and rotating the closure back and forth to advance the indicator mechanism, without actually removing the closure from the container.

It is another object of this invention to provide a device that has positive control of the index member during both the opening and the closing motions and to require the advancement of the index member by one and only one new index during each complete opening and closing cycle.

Yet another object of the invention is to provide an audible sound to confirm that the device has been rotated sufficiently to move the index to the next location and to also provide an audible sound when the device has been rotated sufficiently to re-cock the device for the next open-close sequence.

Still another object is to provide space within the device for the locking mechanisms to slide past each other when not engaged to allow such mechanisms to work reliably over a long period of time.

Another object of the present invention is to combine functions usually requiring several components into single components to reduce the complexity of the device and provide ease of manufacturability and assembly using standard injection molding and assembly techniques.

Another object of the present invention is to provide an indicator assembly that can easily be fitted to an ordinary container without requiring any special modifications to the container itself.

Another object is to provide a device with indicator symbols that can be sensed by touch such as raised letters or braille.

Another object is to provide a device that can be easily grasped by elderly or impaired patients, as by including grasp-facilitating elements on the device.

Another object is to provide a device which is easily manufactured and assembled with a minimum of parts.

The present invention need not include all the objects mentioned above, and may also include other objects not mentioned above. The objects in a preferred embodiment are achieved with a closure having an indicator mechanism and an indicator mechanism actuator which actuates the indicator mechanism only upon an application of an external force urging the closure and container together or apart.

BRIEF DESCRIPTION OF THE DRAWINGS

FIG. 1 is a pictorial view of a closure of the present invention mounted onto a container.

FIG. 2 is an exploded pictorial view of the components of the present invention and a container for the mounting of such components.

FIG. 2A is a partial sectional side view of the center of the device of FIG. 2.

FIG. 3 is a side elevational view of the interior of the skirt of the outer cover of the invention, showing a groove therein.

FIG. 4 is a sectional view of the outer cover of the invention, taken along line 4—4 of FIG. 2.

DETAILED DESCRIPTION OF THE INVENTION

Figure 5:
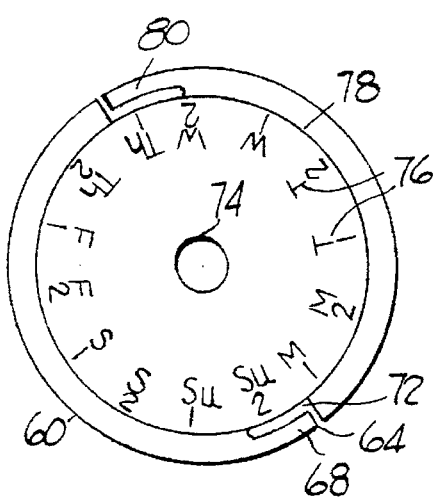
FIG. 5 is a plan view of the indicator wheel of the invention, taken along line 5—5 of FIG. 2.

A pictorial view of a medicine container with a closure 14 in accordance with the present invention is shown in FIG. 1. The closure 14 includes an outer cover 20 having a window 22 therethrough to view indicator symbols on an indicator symbol carrier such as an indicator wheel 60 (see FIG. 2) nested inside the outer cover 20. The clockwise and counterclockwise rotation of the closure cover 14 in relation to the container 12 to close and open the container causes rotation of the outer cover 20 in relation to the indicator wheel 60, thereby advancing the window 22 through the individual indicator symbols on the indicator wheel in the manner described in detail below.

An exploded pictorial view showing details of the closure is in FIG. 2. A principal element of the closure is an indicator mechanism that operates to provide an indication that the closure has been removed from or replaced onto the container. In the preferred embodiment shown, the indicator mechanism includes an outer cover 20, an indicator wheel 60, and a retainer 110. The indicator mechanism is engaged with a sealing cap 150 which has threads 158 to mate with the threads 182 on the neck of a container 180.

The outer cover 20 includes a top portion 21 and a depending skirt 24. In the interior of the outer cap on the bottom surface of the top portion 21 and extending around the periphery of that surface where it joins the skirt 24 is a set of teeth 26. Each tooth 26 has an inclined portion on one side and an edge so that the indicator wheel upper pawl described below can slide over the inclined portion and over the edge to function as a one-way ratchet.

Around the interior surface of the skirt 24 is a set of grooves 28 that are recessed into, but not extending through, the surface and which extend circumferentially around the skirt 24. As better shown in FIG. 3, each groove 28 includes a circumferential portion 30 and a notch portion 32. One end of the notch portion 32 is bounded by a notch wall 33 and the other end of the notch portion 32 joins the circumferential portion 30. Between the notch portion 32 and the circumferential portion 30 is a notch edge 34. Around the bottom of the skirt 24 on the interior side is a radially extending lip 40 which retains the sealing cap 150 along with the indicator wheel 60 and retainer 110. The radially extending lip 40 and also a groove 28 can also be seen in the sectional view of FIG. 4. In the center of the interior surface of the top portion 21 is a downwardly extending hub 48 having the configuration described below in connection with FIG. 2A.

Referring again to FIG. 2, the bottom surface of the indicator wheel 60 is shown. The indicator wheel 60 has an upper pawl 64 on the upper surface to mate with the outer cover teeth 26. The upper pawl 64 is also shown in the plan view of the indicator wheel 60 of FIG. 5 taken along line 5—5 of FIG. 2. The upper pawl 64 is at the end of a finger 68 attached to the indicator wheel 60 at its base 70 and nesting into a recess 72. Therefore, the finger 68 is spaced apart from the indicator wheel 60 except where it attaches to the indicator wheel 60 at its base 70. The finger is preferably flexible (such as being made of a flexible injection moldable plastic) so that the finger 68 flexes up and down in the recess 72 as the upper pawl rides over the teeth 26 of the outer cover 20. Although only one upper pawl 64 is shown in the embodiment of FIG. 2, it will be apparent that several such pawls could be spaced around the indicator wheel to stabilize the engagement of the indicator wheel 60 with the outer cover 20.

In the center of the indicator wheel 60 is a hole 74. The hole 74 receives the outer cover hub 48 to ensure that the indicator wheel 60 stays concentric with the outer cover 20 as shown in more detail in FIG. 2A and explained below. The upper surface of the indicator wheel 60, which is best shown in FIG. 5 taken along line 5—5 of FIG. 2, includes a set of indicator symbols 76 arranged in a circle concentric with the indicator wheel itself. The indicator symbols 76 in the preferred embodiment are abbreviations for doses of medication to be taken on days of the week. For example, the indicator symbols 76 shown in FIG. 5 are "M1, M2, Tu1, Tu2, W1 . . ." for medicine to be taken twice a day. The "M1" indicates the first dose on Monday, the "M2" indicates the second dose on Monday, the "Tu1" indicates the first dose on Tuesday, and so on. The indicator symbols may be printed or molded directly onto the indicator wheel 60 or may instead be printed onto a label 78 which is adhered to the indicator wheel 60 as shown in FIG. 5.

Referring again to FIG. 2, the bottom of the indicator wheel 60 has a lower pawl 80. The lower pawl 80 has a configuration and fits into a recess essentially the same as the upper pawl 64, but the lower pawl 80 points downward to mate with the retainer teeth on the retainer 110 in the manner described below.

The retainer 110 shown in FIG. 2 is a disk-shaped element having a hub 112 on the center of its upper surface to engage the hub 48 of the outer cover 20 as explained below. Also on the upper surface of the retainer 110 is a set of retainer teeth 114 extending upwardly and around the periphery of the retainer. The retainer teeth 114 are similar to the outer cover teeth 26, in that each tooth 114 has an inclined side and an edge whereby the lower pawl 80 of the indicator wheel can flex as it rides over the inclined portion and snap over the edge, to constitute a one-way ratchet. Around the edge of the retainer 110 is at least one radially extending tab 116 to engage the outer cover grooves 28. The tabs 116 extend radially sufficiently to securely engage the outer cover grooves 28 and have a circumferential dimension of approximately the circumferential dimension of the notches 32 of the outer cover grooves 28. Thus, when the tabs 116 are in the notches 32, they fit snugly therein and allow no side to side movement and consequently allow no relative rotation of the outer cover 20 and retainer 110. It will be apparent that the retainer tabs 116 and outer cover notches 28 could be reversed so that the tabs are on the outer cover 20 while the notches are on the retainer 110.

This relation between the outer cover 20 and retainer 110 through the retainer tabs 110 and outer cover groove notches 32 acts as an actuator for the indicator mechanism. The indicator mechanism can be operated or "actuated" only by applying the necessary force between the closure and the container to disengage the retainer tabs 116 from the notches 32.

Figure 6:
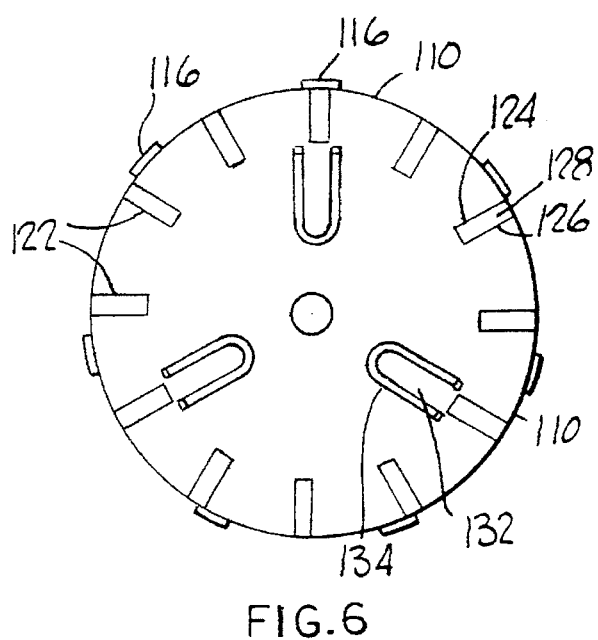
FIG. 6 is a view of the bottom of the retainer of the invention, taken along line 6—6 of FIG. 2.
Figure 7:
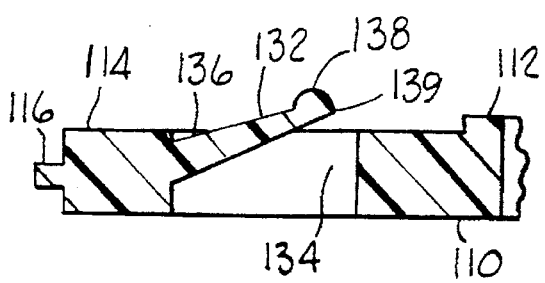
FIG. 7 is a sectional view of a portion of the container of the present invention, taken along line 7—7 of FIG. 2.

Also on the upper surface of the retainer 110 are a set of leaf springs 132, three in the embodiment shown. As better shown in FIG. 6 showing a plan view of the retainer 110 taken along line 6—6 of FIG. 2 and FIG. 7 showing a side partial sectional view of the retainer taken along line 7—7 of FIG. 2, each leaf spring 132 is positioned within a cutout 134 in the retainer 110 and extends upwardly from the base 136 of the leaf spring 132 to the end 138 which is positioned above the upper surface of the retainer 110 when the leaf spring is in its relaxed state. The end 138 of the leaf spring has a protruding spherical tip 139 to ride along the surface of the indicator wheel 60 when the device is assembled and to urge the retainer 110 apart from the outer cover 20 and indicator wheel 60 as explained below.

On the bottom surface of the retainer 110 are a set of retainer protrusions 122 spaced around the periphery, which are better shown in the plan view of the lower surface of the retainer in FIG. 6. Each retainer protrusion 122 extends radially to the periphery of the retainer 110 and has two substantially parallel sides 124 and 126 which extend axially from the lower surface of the retainer 110 to the bottom 128 of the retainer protrusion 122. The retainer protrusions releasably engage the sealing cap protrusions 160 in the sealing cap 150 in the manner described below. Also on the bottom of the retainer 110 is a recess 113 to receive the sealing cap hub 153 in the manner described below in connection with FIG. 2A.

Figure 8:
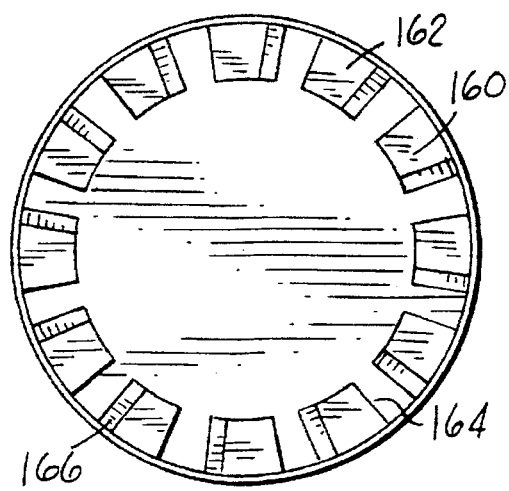
FIG. 8 is a plan view of the sealing cap of the invention, taken along line 8—8 of FIG. 2.

The sealing cap 150 is a cup-shaped element having a top 152 and a depending skirt 154. On the interior of the depending skirt 154 are a set of threads 158 to engage mating threads 182 on the neck of the container 180. On the upper surface of the top 152 are a set of sealing cap protrusions 160 to releasably engage the retainer protrusions 122 in the manner described below. The sealing cap protrusions are also shown in a top plan view in FIG. 8. Each sealing cap protrusion 160 includes a substantially flat top 162 parallel to the top surface of the sealing cap 150, a side 164 perpendicular to the surface of the sealing cap 150 and to flat top 164, and a ramp 166 which is inclined from the surface of the sealing cap 150 to the flat top 162. Each sealing cap protrusion 160 is roughly trapezoidal in plan view, with the side 164 and ramp 166 converging along radial lines toward the center of the retainer 110. The sealing cap 150 also includes a hub 153 which mates with the retainer recess 113 as described below with reference to FIG. 2A.

Figure 9:
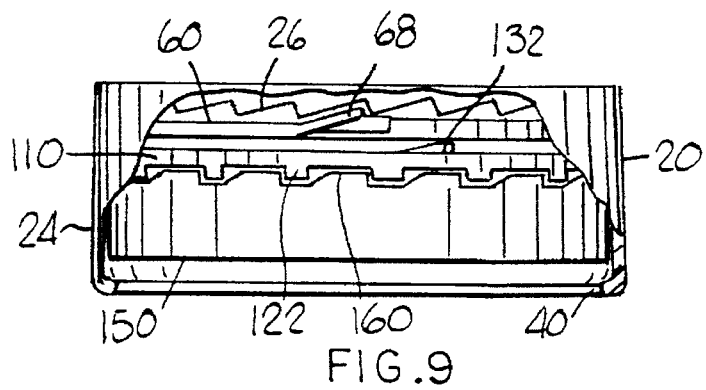
FIG. 9 is a cut-away elevational view of the assembled invention.

The device is assembled such that the indicator wheel 60, retainer 110, and sealing cap 150 are stacked together and nested inside the outer cover 20 as shown in the side elevational and cutaway view of FIG. 9. The indicator wheel upper pawl 64 engages the outer cover teeth 26 and the indicator wheel lower pawl 80 engages the retainer teeth 114. The indicator wheel hole 74 receives the outer cover hub 48 from the top side and receives the retainer hub 112 from the bottom side. The stacked assembly of the indicator wheel 60, retainer 110 and sealing cap 150 are held in nested configuration within the outer cover 20 by the outer cover lip 40 extending around the bottom of the outer cover skirt 24.

With reference as to FIG. 2A, it can be seen how the elements of the devices are held stably together to allow relative rotation but a minimum of side to side movement. The outer cover hub 48 extends downward and into the indicator wheel hole 74. The retainer hub 112 extends upward and is received by a recess 49 in the outer cover hub 48. The sealing cap hub 153 extends upward and is received by the retainer recess 113.

The retainer tabs 116 are received by the outer cover grooves 28. Because the circumferential dimension of the grooves 28 is greater than the circumferential dimension of the tabs 116, there is a limited amount of circumferential movement of the tabs within the grooves, thereby allowing limited rotation of the outer cover relative to the retainer. However, the retainer 110 is urged apart from the indicator wheel 60 and the outer cover 20 by the leaf springs 132 on the retainer. The biasing force of the leaf springs 132 against the lower surface of the indicator wheel 60 drives the retainer 110 downward in relation to the outer cover 20 and indicator wheel 60. This causes the retainer tabs 116 to drop into the notch portion 32 of the outer cover grooves 28. Because the tabs 116 fit snugly within the notches 32 with no play from side to side, rotation of the outer cover 20 relative to the retainer 110 is precluded in that condition.

The retainer protrusions 122 on the bottom side of the retainer 110 rest between the sealing cap protrusions 160 on the upper surface of the sealing cap 150, as best shown in FIG. 9. It can be appreciated that rotation of the sealing cap 150 in the clockwise direction (viewed from above) causes a side 124 (see FIG. 6) of the retainer protrusions 122 to bear against a side 164 (see FIG. 8) of the sealing cap protrusion 160. Because both those sides are approximately parallel to the axis of rotation, the rotational force of the retainer 110 is transferred to the sealing cap 150 through these two sides, thereby causing the sealing cap to rotate clockwise to thread onto and seal the container 180.

Rotating the sealing cap counter-clockwise causes a side 126 (see FIG. 6) of the retainer protrusions 122 to bear against the inclined side 166 of the sealing cap protrusions 160. Because bearing surface of inclined side 166 is not parallel to the axis of rotation, the retainer protrusions 122 tend to ride up on the inclined sides 166 of the sealing cap protrusions 160. As the retainer protrusions ride up on the inclined sides 166 of the sealing cap protrusions 160, the assembly of the retainer 110, indicator wheel 60 and outer cover 20 are driven upward and away from the sealing cap.

Eventually, the retainer protrusions 122 ride all the way up the inclined sides 166 of the sealing cap protrusions 160 to the point where the retainer protrusions press onto the flat tops 162 of the sealing cap protrusions and slide past the sealing cap protrusions altogether. The retainer protrusions 122 then slip back into a space between the sealing cap protrusions 160, and begin riding up the inclined side 166 of the next sealing cap protrusion.

The retainer 110 is prevented from slipping past the sealing cap 150 by applying a force urging the retainer toward the sealing cap to overcome the force that tends to separate the two when the rotational force applied to the retainer is translated into a separating force by the inclined sides 166 of the sealing cap protrusions 160. Because the retainer is assembled with the outer cover by the engagement of the retainer tabs 116 in the outer cover grooves 28, this force is actually applied to the outer cover 20 and transferred to the retainer 110 through the tabs and grooves. Thus the retainer protrusions 122 are forced to bear against the inclined sides 166 of the sealing cap protrusions 160 by this force urging the retainer 110 against the sealing cap 150, so that the counter-clockwise rotational force on the retainer is transferred to the sealing cap 150 to unthread the sealing cap from the container. It is believed in the industry that children are less able to simultaneously rotate the device and apply a force urging the device toward the container than are adults, and so the device is resistant to being removed from the container by a child.

Next described is the operation of the indicator mechanism of the outer cover 20, indicator wheel 60 and retainer 110. It is assumed that initially the tabs 116 of the retainer 110 are positioned in the clockwise end of the outer cover grooves 28. If the outer cover 20 is rotated clockwise as if to screw the sealing cap 150 onto the container 180, the retainer protrusions 122 engage the sealing cap protrusions 160 in the manner described above and cause the sealing cap 150 to thread onto the container 180. This is the result of clockwise rotation of the outer cover 20 regardless of whether a force is applied urging the outer cover 20 toward the container 180, since the retainer protrusions 122 engage the perpendicular sides 164 of the sealing cap protrusions and so no force is necessary to maintain that engagement.

When the sealing cap 150 is completely threaded onto the container 180 so that the resistance to further rotation of the sealing cap exceeds the frictional resistance to the retainer tabs 122 sliding through the outer cover grooves 28, the sealing cap 150 and hence the retainer 110 stop rotating and the outer cover 20 continues to rotate so that the retainer tabs 122 slide through the outer cover grooves 28. When the retainer tabs 122 slide the entire circumferential length of the outer cover grooves 28 so that they abut against the end wall 33 of the groove notches 32, the biasing force of the retainer leaf springs 132 which urges the retainer 110 downward and away from the top 21 of the outer cover causes the retainer tabs 116 to drop into the outer cover notches 32. This results in the retainer 110 descending downward to separate the retainer 110 from the combination of the indicator wheel 60 and outer cover 20. Once the retainer tabs 116 are dropped into the outer cover notches 32 by the biasing force of the leaf springs 132, they are locked therein so that relative movement between the outer cover 20 and retainer 110 is precluded until a force is applied urging the outer cover toward the container to overcome the biasing force of the retainer leaf springs 132 and lift the retainer tabs 116 out of the outer cover notches 32 and into the circumferential portion 30 of the grooves 28 in the manner described below.

As the retainer tabs 116 slide through the circumferential length of the outer cover grooves 28 due to the relative rotation between the outer cover 20 and retainer 110, it can be appreciated that the indicator wheel 60 rotates with the outer cover 20 rather than remaining stationary with the retainer 110. This is because the upper pawl 64 of the indicator wheel 60 is engaged by the teeth 26 of the outer cover 20. The effect of the indicator wheel upper pawl 64 acting on the outer cover teeth 26 is a one-way ratchet; the outer cover 20 can rotate counter-clockwise but not clockwise (viewed from above) in relation to the stationary indicator wheel 60. Because the indicator wheel 60 rotates with the outer cover 20 while the retainer 110 remains stationary, there is relative rotation between the indicator wheel 60 and the retainer 110. Specifically, the indicator wheel rotates clockwise (viewed from above) in relation to the retainer 110.

This clockwise rotation of the indicator wheel 60 over the retainer 110 causes the lower pawl 80 of the indicator wheel 60 to pass over a tooth 114 of the retainer 110. This is accomplished by the indicator wheel lower pawl 80 flexing upward as it rides up and over the ramp of the tooth. When it reaches the edge of the tooth, it pops back down onto the ramp of the next tooth. This abrupt pop produces an audible "click" which confirms to the user that there has been the desired relative rotation between the outer cover 20 and the retainer 110 through the "lost motion" of the retainer tabs 116 sliding through the outer cover grooves 28. This lost motion movement is necessary to position the retainer tabs 116 at the opposite end of the outer cover grooves 28 so that lost motion in the opposite direction can occur to advance the outer cover window 22 past the indictor symbols 76 of the indicator wheel 60 in the manner described below.

It should be appreciated that the purpose of the leaf springs 132 on the retainer 110 are to bias the retainer 110 away from the outer cover 20 so that the retainer tabs 116 drop into the outer cover notches 32, and that this function could be accomplished through other means. In particular, it could be accomplished by designing the lower pawl 80 of the indicator wheel 60 and the teeth 114 of the retainer 110 such that the lower pawl 80 sufficiently protrudes below the bottom surface of the indicator wheel 60 so that it biases the retainer 110 downward. This could be enhanced by including a plurality of such lower pawls around the periphery of the indicator wheel lower surface to provide a uniform axial biasing force against the retainer.

When the outer cover is rotated counter-clockwise (viewed from above) as if to unthread the sealing cap 150 from the container 180, the indicator mechanism (comprising the outer cover 20, indicator wheel 60 and retainer 110 in this embodiment) does not operate unless a simultaneous force is applied urging the outer cover 20 toward the container 180. As explained above, if no such force is applied the combination of outer cover 20, indicator wheel 60 and retainer 110 simply rotate relative to the stationary sealing cap 150 because the retainer protrusions 122 ride over the inclined sides 166 of the sealing cap protrusions 160. In addition, there is no relative movement among the outer cover 20, indicator wheel 60 and retainer 110, because the retainer tabs 116 are locked into the outer cover notches 32.

Once a force is applied urging the outer cover 20 toward the container 180 at the same time that a rotative force is applied turning the outer cover 20 in the counter-clockwise direction, the mechanism operates as follows. The force pushes the outer cover 20 downward toward the retainer 110 so that the retainer tabs 116 move upward in the outer cover notches 32. When the retainer tabs 116 reach the top of the outer cover notches 32, the retainer tabs are free to slide through the circumferential portion 30 of the outer cover grooves 28. Therefore, the outer cover 20 rotates counter-clockwise while the retainer 110 is held stationary by its engagement with the sealing cap 150. The sealing cap 150 in turn is held stationary by the friction of the tightened threads of the sealing cap 10 on the container threads 182.

As the outer cover 20 rotates counter-clockwise and the retainer 110 is held stationary, the indicator wheel 60 is held stationary with the retainer 110. This is because the lower pawl 80 of the indicator wheel is prevented from moving by its engagement with the teeth 114 of the retainer 110. The rotation of the outer cover 20 relative to the indicator wheel 60 causes the outer cover window 22 to move to a new indicator symbol 76 on the indicator wheel 60. At the same time, a tooth 26 of the outer cover 20 passes over the indicator wheel upper pawl 68 to produce an audible "click" to confirm the proper advancement of the window 22.

When the retainer tabs 116 slide all the way to the end wall 35 of the outer cover grooves, the outer cover 20 can no longer rotate relative to the retainer 110. Further counter-clockwise rotation of the outer cover 20 causes the retainer 110 to rotate as well. This rotation overcomes the frictional resistance of the threads of the sealing cap 150 engaged with the container 180, and thereby unthreads the sealing cap from the container. As explained above, however, this requires continuous application of a force urging the outer cover 20 toward the container 180 to prevent the retainer 110 from sliding past the sealing cap 150.

When the sealing cap 150 is fully unthreaded and removed from the container 180, the device is once again ready to be threaded back onto the container. The rethreading of the closure onto the container abuts the retainer tabs 116 against the end wall 35 of the outer cover grooves 28. The process described in the paragraphs above is repeated to once again unthread the closure from the container.

One of the notable advantages of this design is that, unless a force is applied urging the outer cover 20 toward the container 180, the indicator mechanism cannot be advanced. Therefore, it is difficult to accidentally advance the indicator mechanism. Further, unless such force is applied, the closure cannot be removed from the container. Thus, the deliberate force that is required in order to advance the indicator mechanism is the same deliberate force required to remove the closure from the container.

It may be desirable to dimension the elements of the closure such that a counterclockwise rotation of the closure as if to unthread it from the container, without applying the requisite force to the closure urging it toward the container, causes an audible warning to alert adults that children may be playing with the device. This can be accomplished by making the skirt 154 of the sealing cap 150 sufficiently long in relation to the distance from the outer cap top interior to the outer cap annular ring 40, that the leaf springs 132 on the retainer 110 must compress in order for the retainer protrusions 122 to pass over the sealing cap protrusions 160. Thus the leaf springs 132 compress as the retainer protrusions 122 ride up and over the sealing cap protrusions 160. When the retainer protrusions 122 pass over the sealing cap protrusions 160, the force of the compressed leaf springs 132 cause the retainer 110 to abruptly snap down onto the sealing cap 150 to produce an audible click. A counterclockwise turning of the closure as if to unthread the closure from the container 180 causes the retainer protrusions 122 to repeatedly ride over the sealing cap protrusions 160 to produce a series of clicks. This alerts adults in the vicinity that a child may be playing with the device. It is important in this embodiment that the force exerted by the compressed leaf springs 132 be less than the force necessary to maintain the engagement between the retainer protrusions 122 and sealing cap protrusion 160. Otherwise, the force of the leaf springs 132 will maintain the engagement between the retainer protrusions 122 and sealing cap protrusions 160 so that the sealing cap unthreads from the container, even without affirmatively applying a force urging the closure toward the container.

Another benefit to the arrangement described above in which the retainer leaf springs 132 urge the retainer 110 toward the sealing cap 150, is that it is not necessary to apply a force urging the closure toward the container to maintain an engagement between the retainer protrusions 122 and sealing cap protrusions 160 when threading the closure onto the container. Instead, the leaf springs 132 depress the retainer 110 onto the sealing cap 150 so that the retainer protrusions 122 maintain engagement with the sealing cap protrusions 160. In contrast with the situation when the closure is turned counterclockwise to remove it from the container, when the closure is rotated clockwise to thread it onto the container this engagement is maintained without the necessity for applying a force urging the closure toward the container. This is because the sides of the sealing cap protrusions 160 that bear against the retainer protrusions 122 when the closure is rotated counterclockwise to remove the closure from the container are the inclined sides 166, while the sides of the sealing cap protrusions 160 that bear against the retainer protrusions 122 when the closure is rotated clockwise to thread the closure back onto the container are the perpendicular sides 164.

It can be appreciated that there is frictional resistance between the various moving parts of the device. Preferably, the magnitude of the various frictional forces produced by this resistance is proportioned to facilitate the proper operation of the device. The device should ideally be constructed such that the frictional force between the retainer protrusions 122 and the inclined sides 166 of the sealing cap protrusions 160, which tends to engage the retainer 110 with the sealing cap 150, should be less than the frictional resistance between the threads 158 of the cap 150 and the container, which resists the unscrewing of the cap from the threads 182 of the container 180 to open it when the device has been tightened onto the container 180. Therefore, by rotating the device counter-clockwise to unscrew it from the container 180 to open the container, the indicator mechanism (comprising the outer cover 20, indicator wheel 60 and retainer 110) merely rotates while the sealing cap 150 remains stationary on the container 180. The sliding of the retainer protrusions 122 over the sealing cap protrusions 160 produces a series of "clicks" to alert the user that the closure is not being properly operated to remove it from the container. This rotation continues until the user applies a force urging the device toward the container 180 in order to increase the frictional force between the retainer protrusions 122 and sealing cap protrusions 160 and thereby increase the rotational force on the sealing cap 150. This causes the rotation of the retainer 110 to be translated into rotation of the sealing cap 150 so that the sealing cap 150 unthreads from the container 180 to open it.

Similarly, the frictional force between the outer cover 20, and the rest of the indicator mechanism (which includes the friction between the outer cover teeth 26 and the indicator wheel upper pawl 68 which tends to maintain the outer cover 20 and indicator wheel 60 in engagement, plus the friction between the outer cover grooves 28 and the retainer tabs 116 which tends to maintain the outer cover 20 and retainer 110 in engagement) should be less than the frictional force between the sealing cap threads 158 and container threads 182 when the cap is tightened onto the container which resists the unscrewing of the cap from the container. Therefore, once the user applies a force urging the device toward the container 180, the friction between the retainer protrusions 122 and the sealing cap protrusions 160 causes the retainer 110 and sealing cap 150 to be engaged. At the same time, this force urging the device toward the container causes the retainer tabs 116 to move into the circumferential portion 30 of the grooves 28 of the outer cover 20 so that the retainer tabs 116 are free to slide in the circumferential portion 30. The rotation of the outer cover 20 at this point produces, first, rotation of the outer cover 20 in relation to the stationary indicator wheel 60 in order to advance the outer cover window 22 to a new indicator wheel symbol, which also results in an audible "click" as the indicator wheel upper pawl 68 passes over one of the teeth 26 of the outer cover 20 and, second, rotation of the entire assembly of outer cover 20, radiator wheel 60, retainer 110 and sealing cap 150 so that the device unscrews from the container 180 to open it.

It can be appreciated that this relationship among the frictional components ensures that unless the requisite force is applied urging the device toward the container it is not possible to remove the sealing cap from the container or to advance the outer cover window to a new indicator wheel symbol. Thus, a single step—that of applying such force—accomplishes the dual purpose allowing the container to be opened and allowing the indicator symbol to advance to record such opening. If that force is not applied, it is impossible to open the container and it is also impossible to indicate such opening by advancement of the symbol. Therefore, the user is unlikely to inadvertently advance the symbol without opening the container.

It is also preferable that the friction between the indicator wheel lower pawl 80 and the retainer teeth 114 which tends to maintain the indicator wheel 60 and retainer 110 in engagement be sufficiently high such that a clockwise rotation applied to the outer cover 20 is translated into rotation of the sealing cap 150 without any relative rotation of the outer cover 20 with respect to the sealing cap 150, until the sealing cap 150 is tightened onto the container 180. The degree of tightening of the sealing cap 150 onto the container is such that the resulting friction between the threads 154 of the sealing cap 150 and the threads 182 of the container 180 which resists unscrewing the cap from the container is of a magnitude described above (that is, it is greater than the friction between the retainer protrusions 122 and the sealing cap protrusions 160). Once this minimum degree of tightening of the sealing cap 150 onto the container 180 is achieved, the further rotation of the outer cover 20 causes the outer cover 20 and indicator wheel 60 to rotate while the retainer 110 and sealing cap 150 remain stationary. This causes lower pawl 80 of the indicator wheel 60 to pass over a tooth 114 of the retainer 110 to produce an audible "click" confirming that the device has been sufficiently tightened onto the container 180 and to recocking the indicator mechanism by sliding the retainer tabs 116 through the length of the outer cover grooves 28. The pawl 80 passes over only one tooth 114, because as it passes the retainer tabs 116 travel through the outer cover grooves 28; when the tabs 116 reach the end of a groove 28, the pawl 80 has passed over one tooth 114 and no further travel is possible.

It can be appreciated that the tolerances, materials and spring forces of the device may be adjusted by a person skilled in the art as necessary to achieve the frictional relationships described above.

It may also be desirable to include orientation features on the components to facilitate their manufacture, handling and assembly. For example, the retainer may have a center post on one side but not the other to ensure it is assembled right side up on the device, the retainer may have one or more alignment grooves or depressions on its circumference; the outer cover may have ribs extending from top to bottom to facilitate the grasping of the device with one or more interruptions on the ribs to aid in orienting the device and a bead on the bottom radially inner edge of the outer cover 20 to hold the device together may have cut-outs to allow the tabs 116 of the retainer 110 to pass for assembly purposes.

Although the preferred embodiments described above are described in the context of a threaded closure and container, it will be apparent that the invention could also be utilized with bayonet-type closures in which one of the closure and the container has a set of bayonet lugs and the other has a set of mating lugs so that it is necessary to urge the closure toward the container while applying a rotative force in order to disengage the bayonet lugs from the mating lugs to remove the closure from the container. The invention may also be utilized in systems where the closure is removed from the container by unsnapping it from the container.

What is claimed is:

1. A closure for a container to indicate the removal or replacement of the closure on the container, comprising: an indicator mechanism; and an indicator mechanism actuator which actuates the indicator mechanism only upon an application of an external force urging the closure toward or away from the container;

a cap attachable and detachable to the container to close the container, the cap being detachable from the container only upon said application of said external force;

the cap being engageable and disengageable with the indicator mechanism, the cap being engageable with the indicator mechanism to detach the cap from the container only upon said application of said external force;

the cap being rotatably attached to the indicator mechanism, one of the indicator mechanism and cap including protrusions and the other of the indicator mechanism and cap including mating protrusions to releasably engage with the protrusions, and the indicator mechanism including a spring to apply an internal force urging at least part of the indicator mechanism toward the cap so that when attaching the cap to the container the protrusions mate with the mating protrusions and the indicator mechanism engages the cap;

the protrusions and mating protrusions being configured such that the spring exerts sufficient internal force to maintain the protrusions and mating protrusions in engagement when attaching the cap to the container but the spring does not exert sufficient internal force to maintain the protrusions and mating protrusions in engagement when detaching the cap from the container, so that an additional external force must be applied between the indicator mechanism and the cap to maintain the protrusions and mating protrusions in engagement when detaching the cap from the container;

the indicator mechanism including an outer cover having a top and an outer cover depending skirt; an indicator wheel positioned below the outer cover and rotatably engaged with the outer cover; indication symbols on one of the outer cover and indicator wheel and an indicator to indicate said symbols on the other of the outer cover and indicator wheel; and a retainer positioned below the indicator wheel and rotatably engaged with the indicator wheel;

the retainer being engaged with the counter cover to allow limited rotation of the outer cover in relation to the retainer;

one of the retainer and outer cover including a set of limited motion grooves and the other of the outer cover and retainer including a set of mating limited motion tabs, whereby the outer cover can rotate a limited degree in relation to the retainer by the limited motion tabs sliding through the limited motion grooves.

2. The closure of claim 1 wherein the limited motion grooves include a tab lock to prevent sliding of the limited motion tabs in the limited motion grooves until the application of said external force.

3. The closure of claim 2, wherein the limited motion grooves have a first end and a second end opposite the first end and a groove length between the first end and second end for accepting the limited motion tabs, and the limited motion tabs have a first end and a second end opposite the first end and a tab body between the first end and second end, the tab body being shorter than the groove length so that the limited motion tabs can slide through the limited motion grooves.

4. The closure of claim 3, wherein the tab lock is a portion of the groove length that is widened to receive the limited motion tabs.

5. A closure for a container to indicate the removal or replacement of the closure on the container, comprising: an indicator mechanism; and an indicator mechanism actuator which actuates the indicator mechanism only upon an application of an external force urging the closure toward or away from the container;

a cap attachable and detachable to the container to close the container, the cap being detachable from the container only upon said application of said external force;

the cap being engageable and disengageable with the indicator mechanism, the cap being engageable with the indicator mechanism to detach the cap from the container only upon said application of said external force;

the cap being rotatably attached to the indicator mechanism, one of the indicator mechanism and cap including protrusions and the other of the indicator mechanism and cap including mating protrusions to releasably engage with the protrusions, and the indicator mechanism including a spring to apply an internal force urging at least part of the indicator mechanism toward the cap so that when attaching the cap to the container the protrusions mate with the mating protrusions and the indicator mechanism engages the cap;

the protrusions and mating protrusions being configured such that the spring exerts sufficient internal force to maintain the protrusions and mating protrusions in engagement when attaching the cap to the container but the spring does not exert sufficient internal force to maintain the protrusions and mating protrusions in engagement when detaching the cap from the container, so that an additional external force must be applied between the indicator mechanism and the cap to maintain the protrusions and mating protrusions in engagement when detaching the cap from the container;

the indicator mechanism including an outer cover having a top and an outer cover depending skirt; an indicator wheel positioned below the outer cover and rotatably engaged with the outer cover; indication symbols on one of the outer cover and indicator wheel and an indicator to indicate said symbols on the other of the outer cover and indicator wheel; and a retainer positioned below the indicator wheel and rotatably engaged with the indicator wheel; and the spring including at least one leaf spring on the retainer urging the retainer away from the indicator wheel and toward the cap.

6. The closure of claim 5, wherein the leaf spring is positioned within a cutout in the retainer so that the leaf spring can flex into the cutout.

7. The closure of claim 6, wherein there are a plurality of leaf springs circumferentially spaced on the retainer.

8. A closure for a container to indicate the removal or replacement of the closure on the container, comprising: an indicator mechanism; and an indicator mechanism actuator which actuates the indicator mechanism only upon an application of an external force urging the closure toward or away from the container;

a cap attachable and detachable to the container to close the container, the cap being detachable from the container only upon said application of said external force;

the cap being engageable and disengageable with the indicator mechanism, the cap being engageable with the indicator mechanism to detach the cap from the container only upon said application of said external force;

the cap being rotatably attached to the indicator mechanism, one of the indicator mechanism and cap including protrusions and the other of the indicator mechanism and cap including mating protrusions to releasably engage with the protrusions, and the indicator mechanism including a spring to apply an internal force urging at least part of the indicator mechanism toward the cap so that when attaching the cap to the container the protrusions mate with the mating protrusions and the indicator mechanism engages the cap;

the protrusions and mating protrusions being configured such that the spring exerts sufficient internal force to maintain the protrusions and mating protrusions in engagement when attaching the cap to the container but the spring does not exert sufficient internal force to maintain the protrusions and mating protrusions in engagement when detaching the cap from the container, so that an additional external force must be applied between the indicator mechanism and the cap to maintain the protrusions and mating protrusions in engagement when detaching the cap from the container;

the indicator mechanism including an outer cover having a top and an outer cover depending skirt; an indicator wheel positioned below the outer cover and rotatably engaged with the outer cover; indication symbols on one of the outer cover and indicator wheel and an indicator to indicate said symbols on the other of the outer cover and indicator wheel; and a retainer positioned below the indicator wheel and rotatably engaged with the indicator wheel;

the cap including a circumferential bottom, and the indicator wheel, container, and cap being held in a nesting relationship with the outer cover by an annular bead extending radially inward from the skirt of the outer cover; and the indicator wheel having a central hole, the outer cover has an outer cover central hub extending into the indicator wheel central hole with a recessed end and the retainer has a retainer central hub extending into the outer cover central hub recess.

9. A closure for a container to indicate the removal or replacement of the closure on the container, comprising: an indicator mechanism; and an indicator mechanism actuator which actuates the indicator mechanism only upon an application of an external force urging the closure toward or away from the container;

a cap attachable and detachable to the container to close the container, the cap being detachable from the container only upon said application of said external force;

the cap being engageable and disengageable with the indicator mechanism, the cap being engageable with the indicator mechanism to detach the cap from the container only upon said application of said external force;

the cap being rotatably attached to the indicator mechanism, one of the indicator mechanism and cap including protrusions and the other of the indicator mechanism and cap including mating protrusions to releasably engage with the protrusions, and the indicator mechanism including a spring to apply an internal force urging at least part of the indicator mechanism toward the cap so that when attaching the cap to the container the protrusions mate with the mating protrusions and the indicator mechanism engages the cap;

the protrusions and mating protrusions being configured such that the spring exerts sufficient internal force to maintain the protrusions and mating protrusions in engagement when attaching the cap to the container but the spring does not exert sufficient internal force to maintain the protrusions and mating protrusions in engagement when detaching the cap from the container, so that an additional external force must be applied between the indicator mechanism and the cap to maintain the protrusions and mating protrusions in engagement when detaching the cap from the container;

the indicator mechanism including an outer cover having a top and an outer cover depending skirt; an indicator wheel positioned below the outer cover and rotatably engaged with the outer cover; indication symbols on one of the outer cover and indicator wheel and an indicator to indicate said symbols on the other of the outer cover and indicator wheel; and a retainer positioned below the indicator wheel and rotatably engaged with the indicator wheel;

wherein the protrusions are spaced around one of the upper surface of the cap and lower surface of the indicator mechanism, each protrusion having a first side inclined to said surface.

10. The closure of claim 9, wherein each said protrusion has a second side opposite the first side, said second side being substantially perpendicular to said surface, where the protrusion first sides urge the indicator mechanism and cap apart upon rotating said indicator mechanism in a first rotational direction, and the protrusion second sides do not urge the indicator mechanism and cap apart upon rotating said indicator mechanism in a second rotational direction, said second rotational direction being opposite from said first rotational direction.

11. A closure for a container to indicate the removal or replacement of the closure on the container, comprising: an indicator mechanism; and an indicator mechanism actuator which actuates the indicator mechanism only upon an application of an external force urging the closure toward or away from the container;

a cap attachable and detachable to the container to close the container, the cap being detachable from the container only upon said application of said external force;

the cap being engageable and disengageable with the indicator mechanism, the cap being engageable with the indicator mechanism to detach the cap from the container only upon said application of said external force;

wherein the indicator mechanism includes a bottom surface having one of a set of protrusions and mating protrusions and the cap includes a top surface and a depending skirt attached to said top surface, the top surface having the other of a set of protrusions and matching protrusions wherein the protrusions mate the mating protrusions so that the indicator mechanism engages with the closure upon said application of said external force.

12. The closure of claim 11, wherein the cap is detachable from the container by rotating the cap relative to the container in a first direction of rotation, and wherein the cap is attachable to the container by rotating the cap relative to the container in a second direction of rotation opposite the first direction of rotation.

13. The closure of claim 12 wherein the skirt of the cap includes threads and the container includes mating threads so that the cap is threadably attachable to and detachable from the container.

\* \* \* \* \*